United States Patent [19]
Pejaver et al.

[11] Patent Number: 6,100,302
[45] Date of Patent: *Aug. 8, 2000

[54] PROPOFOL FORMULATION WITH ENHANCED MICROBIAL CHARACTERISTICS

[75] Inventors: Satish K. Pejaver, Bridgewater, N.J.; Rajeshwar Motheram, Wilmington, Del.; Barrett E. Rabinow, Skokie, Ill.; Josben C. dela Rosa, Nutley, N.J.

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/286,159

[22] Filed: Apr. 5, 1999

[51] Int. Cl.$^7$ .................................................. A61K 31/05
[52] U.S. Cl. ........................... 514/731; 514/816; 514/938
[58] Field of Search ..................... 514/731, 816, 514/938

[56] References Cited

U.S. PATENT DOCUMENTS 5,688,528  11/1997  Carlsson et al. ...................... 424/450
5,714,520  2/1998  Jones et al. ............................. 514/731

FOREIGN PATENT DOCUMENTS 2731617  9/1996  France .

*Primary Examiner*—Rebecca Cook
*Attorney, Agent, or Firm*—Jeffrey C. Nichols; Mark J. Buonaiuto; Frances C. Kowalik

[57] ABSTRACT

Formulations of intravenous anesthetic propofol emulsions are provided which contain sufficiently low concentrations of soybean oil to produce a stable emulsion and simultaneously provide reduced nutrients, which inhibit microbial growth thereby providing protection against accidental microbial contamination during long-term IV infusions. In addition to the inhibition of microbial growth due to a reduction of nutrients, the formulation exhibits unanticipated additional microbial inhibition due to an increased availability of propofol. The low concentration of soybean oil also provides a formulation that reduces the chances of fat overload when administered over an extended period of time to chronically ill patients.

9 Claims, 1 Drawing Sheet

PROPOFOL FORMULATION WITH ENHANCED MICROBIAL CHARACTERISTICS

FIELD OF THE INVENTION

This invention generally relates to improved pharmaceutical formulations of the intravenous anesthetic propofol with enhanced microbial characteristics. More particularly, this invention relates to an improved propofol emulsion formulation which is bacteriostatic and in certain forms bacteriocidal without the use of preservatives or other antimicrobial agents.

BACKGROUND OF THE INVENTION

Propofol (2,6 diisopropylphenol) is a hydrophobic, water-insoluble oil which is widely used as an anesthetic agent via IV administration. Propofol is generally incorporated in a vegetable oil emulsion to enable intravenous administration.

Sterile pharmaceutical compositions of propofol and their use in inducing anesthesia are generally described in U.S. Pat. Nos. 4,056,635; 4,452,817 and 4,798,846, all to Glen and James. The propofol/soybean oil emulsion has gained widespread use for induction and/or maintenance of anesthesia, for maintenance of monitored anesthesia care and for sedation in the Intensive Care Unit (ICU). It is advantageous in that it possesses both a rapid onset anesthesia and a short recovery time.

One problem associated with the compositions described in the before mentioned patents is the risk of bacterial contamination primarily due to the high soybean oil content, and lack of antimicrobial preservatives.

It has been shown that the propofol emulsion formulated without preservatives will grow bacteria. The oil content, combined with a lack of antimicrobial additives, present a risk of bacterial contamination (Arduino et al., 1991, Sosis & Braverman, 1993; PDR, 1995).

To address the problem of bacterial contamination of propofol emulsions, additional formulations of propofol have been developed. One such formulation, is described in U.S. Pat. No. 5,731,356. It is believed that the product described in that patent is commercially marketed under the tradename DIPRIVAN and comprises a sterile, pyrogen-free oil-in-water emulsion containing 1% (w/v) propofol in 10% (w/v) soybean oil dispersed in water and stabilized by 1.2% (w/v) lecithin phospholipidis and includes a commonly used preservative, EDTA to provide a claimed benefit of less than one log increase in growth of certain gram-positive and gram-negative bacteria over a twenty-four period. Such a formulation, however, requires the administration of EDTA which is a chelating agent that removes cations such as calcium and magnesium. Removal thereof can be dangerous when administered to patients with low calcium or magnesium levels, or who have compromised control systems for those minerals.

A second formulation, described in U.S. Pat. No. 5,637,625, is an oil-free formulation in which, in one described form, the propofol is in a 6.8% wt/wt concentration and dispersed in water as micro-droplets with a diameter generally less than 1 micron, having a phospholipid or monoglyceride outer covering. However, it appears that upon administration this formulation may increase site irritation to an unacceptable level.

The problems described above are substantially reduced if not eliminated by an improved propofol formulation provided in accordance with the present invention.

Propofol emulsions of the present invention do not support the growth of bacteria, and in fact exhibit bacteriostatic properties. An important feature of the present invention is the formulation of a propofol emulsion for intravenous administration with a reduced risk of bacterial growth after site contamination which may occur in a medical care giving setting.

The preferred embodiment of the present invention provides a propofol formulation, preferably an emulsion, having antimicrobial properties without the use of antimicrobial additives and with any additives preferably limited to those generally required to prepare an oil-in-water emulsion formulation.

SUMMARY OF THE INVENTION

In accordance with the present invention, there is provided an improved formulation of propofol for intravenous administration using decreased levels of soybean oil, fats or triglycerides. The formulation preferably consists of phospholipid-coated microdroplets ranging from about 160 to about 200 nanometers in diameter. These microdroplets contain a sphere of propofol a solvent such as vegetable oil, surrounded by a stabilizing layer of a phospholipid. This formulation can safely provide sedation over extended periods of time. The low oil concentration emulsion containing propofol provides a stable oil-in-water emulsion and unexpectedly exhibits antimicrobial properties comparable to higher water imiscible solvent concentration emulsions containing preservatives.

BRIEF DESCRIPTION OF THE DRAWINGS

A more complete understanding of the present invention may be obtained from consideration of the following description in conjunction with the drawing appended hereto, in which.

DETAILED DESCRIPTION OF THE PREFERRED EMBODIMENT OF THE INVENTION

Figure 1:
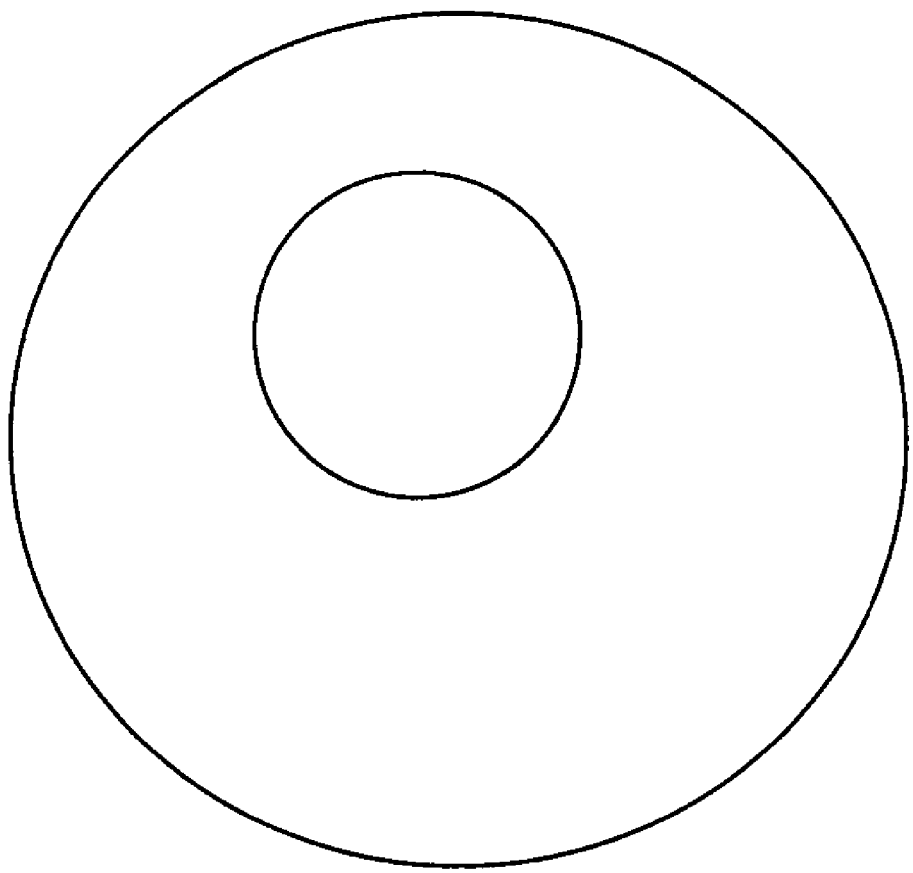
FIG. 1 is a schematic representation of the soybean-oil and lecithin-coated propofol microdroplet.

Accordingly, the present invention provides a sterile pharmaceutical composition for parenteral administration which, in the preferred embodiment, comprises an emulsion in which propofol is dissolved in a water-immiscible solvent, preferably soybean oil and which further comprises a decreased concentration of solvent such that there is a deterrence of significant growth of microorganisms for at least 24 hours, following adventitious, extrinsic contamination. An emulsion being defined as a distinct, two-phase system that is in equilibrium.

Referring to FIG. 1, the composition of the present invention preferably contains a microdroplet, approximately 160 to approximately 200 nanometers in mean diameter, comprised of propofol, dissolved in an oil or other solvent, surrounded by a surfactant, and suspended in a pharmaceutical acceptable injectable carrier.

A wide range of water-immiscible solvents can be used in the compositions of the present invention. Typically, the water-immiscible solvent is a vegetable oil, for example soy bean, safflower, cottonseed, corn, sunflower, arachis, castor or olive oil. Preferably, the vegetable oil is soybean oil. Alternatively, the water-immiscible solvent is an ester of a medium or long-chain fatty acid, for example, a mono-, di-, or triglyceride; or is a chemically modified or manufactured material such as ethyl oleate, isopropyl myristate, isopropyl palmirate, a glycerol ester, polyoxyl hydrogenated castor oil. In a further alternative the water-immiscible solvent may be a marine oil, for example cod liver or another fish-derived oil. Suitable solvents also include fractionated oils, for example, fractionated coconut oil or modified soy bean oil. Furthermore, the compositions of the present invention may comprise a mixture of two or more of the above water-immiscible solvents.

Suitable surfactants include synthetic non-ionic surfactants, for example ethoxylated ethers and esters polypropylene-polyethylene block co-polymers, and phospholipids for example, naturally-occurring phospholipids such as egg and soya phospolipids and modified or artificially manipulated phospholipids (for example prepared by physical fractionation and/or chromatography), or mixtures thereof. Preferred surfactants are egg phospholipids, such as lecithin.

The composition of the present invention may be made isotonic with blood by the incorporation of a suitable tonicity modifier, for example glycerin.

The composition of the pharmaceutically acceptable injectable carrier is preferably a pyrogen free water, or Water for Injection U. S. P.

The formulation of the present invention typically comprises from about 0.1 to about 5%, by weight, preferably 1% to 2% by weight, of propofol. The water-immiscible solvent is suitably present in an amount that is preferably from 0.1–3% by weight of the composition and more suitably from 1–3% by weight of the composition.

Generally, in the formulation of the preferred embodiment of the subject emulsions, propofol, either alone or dissolved in a water-immiscible solvent, is emulsified by means of a surfactant. It is preferred that propofol is dissolved in a water-immiscible solvent prior to emulsification. The propofol dissolved in water immiscible solvent is then mixed with water containing surfactant. The resultant primary emulsion is recirculated through a homogenizer under high pressure, until ideal globule size is achieved. The composition of the present invention is suitably formulated to be at physiologically neutral pH, typically in the range 6.0–8.5, if necessary by means of alkali such as sodium hydroxide.

More particularly, the composition of the present inventions are sterile aqueous formulations and are rendered sterile according to conventional manufacturing techniques using, for example, terminal sterilization by autoclaving.

Example 1

| Quantities | |
|---|---|
| | % (weight) |
| propofol | 1.0 |
| soy bean oil | 1.0–3.0 |
| lecithin | 1.2 |
| glycerin | 2.25 |
| sodium hydroxide | q.s. |
| Water for injections | to 100 |

A sterile aqueous oil-in-water emulsion for parenteral administration was prepared using a preferred method as follows:

1) The oil phase was prepared by adding Propofol (1% by weight) to soybean oil (1%–3% by weight) and stirred until dissolved.
2) Glycerin (2.25% by weight) and Lecithin (1.2% by weight) are added to Water for Injection at 60±10° C. and mixed until a uniform dispersion was formed, constituting the aqueous phase.
3) The oil phase was added to aqueous phase while stirring to form the primary emulsion. The primary emulsion was mixed at 60±10° C. until it became homogenous. The homogenous primary emulsion was cooled, pH adjusted with sodium hydroxide, and final weight adjusted with Water for Injection.
4) The primary emulsion was then recirculated through a high pressure homogenizer and cooler (heat exchange system) until the required mean globule size of the emulsion (approximately 200 nm) was achieved.
5) The resultant oil-in-water emulsion was transferred to a filling vessel. The pH of the emulsion was adjusted if necessary using sodium hydroxide, filtered, filled under nitrogen and steam sterilized.

The compositions of the present invention are useful as anesthetics, which includes sedation and induction and maintenance of general anesthesia. Accordingly, the present invention provides a method of producing anesthesia in a warm-blooded animal, including humans, comprising administering parenterally a sterile aqueous pharmaceutical composition which comprises an oil-in-water emulsion in which propofol, in a water-immiscible solvent, is emulsified with water and stabilized by means of a surfactant. A preferred embodiment being described in Example 1 above.

Dosage levels of propofol for producing general anesthesia, both induction (for example about 2.0–2.5 mg/kg for an adult) and maintenance (for example about 4–12 mg/kg/hr), and for producing a sedative effect (for example 0.3–4.5 mg/kg/hr), may be derived from the substantial body of literature on propofol. Furthermore, the anesthetist and/or physician would modify the dose to achieve the desired effect in any particular patient, in accordance with normal skill in the art.

The present invention provides formulations of the intravenous anesthetic drug propofol (2,6-diisopropylphenol) as a phospholipid-coated microdroplet with substantially decreased levels of fats or triglycerides. The formulation of the present invention is also shown to be bacteriostatic and in some formulations, bactericidal against the particular forms of bacterial contamination found in the health care environment.

Accordingly, in another aspect, the present invention provides an intravenous fat emulsion that comprises a sufficiently decreased amount of soybean oil. It is within the reduction of soybean oil from the industry standard 10% by weight to 1–3% by weight in accordance with the present invention that several unexpected results arise. Such results include, for at least 24 hours, no greater than a ten-fold increase in the growth following contamination with one or more microorganisms, such as *Staphylococcus aureus, Escherichia coli, Pseudomonas aeruginosa* and *Candida albicans*.

The antimicrobial effects of propofol compositions having low soybean oil content is illustrated in the following tables which detail the microbial growth in various propofol formulations. The formulations including microbial growth in 1%, 2% and 3% soybean oil concentrations included in the present invention upon inoculation with 100 cfu/ml (which approximates touch contamination of standard USP test organisms *S. aureus, P. aeruginosa, E. Coli* and *C. albincans*). These effects are contrasted with other propofol formulations including a 10% soybean oil level emulsion and the propofol formulation containing 0.005% EDTA and marketed under the tradename DIPRIVAN. The effects are also contrasted with the growth after inoculation exhibited in a saline solution as represented by the growth numbers in the viability control.

TABLE 1

*S. aureus:* Inoculum Concentration: 2.0 log Nominal

| | Microbial Growth (Log Cfu/mL) | | |
|---|---|---|---|
| Test Preparations | 0 HOUR | 24 HOUR | 48 HOUR |
| 1% Soybean Oil | 1.78 | <1 | <1 |
| 2% Soybean Oil | 1.57 | 1.78 | <1 |
| 3% Soybean Oil | 1.87 | 1.78 | 1.43 |
| 10% Soybean oil (control) | 1.88 | <3.00 | 3.30 |
| Diprivan | 2.00 | 1.20 | 0.75 |
| Viability Control | 1.93 | 1.89 | 1.63 |

TABLE 2

*P. aeruginosa:* Inoculum Concentration: 2.0 Log Nominal

| | Microbial Growth (Log Cfu/mL) | | |
|---|---|---|---|
| Test Preparations | 0 HOUR | 24 HOUR | 48 HOUR |
| 1% Soybean Oil | <1 | <1 | <1 |
| 2% Soybean Oil | 1.00 | <1 | <1 |
| 3% Soybean Oil | 1.00 | <1 | <1 |
| 10% Soybean oil (control) | 1.89 | 4.49 | 6.72 |
| Diprivan | 1.55 | 0.50 | 0.75 |
| Viability Control | 2.08 | 1.92 | 3.85 |

TABLE 3

*E. Coli:* Inoculum Concentration: 2.0 Log Nominal

| | Microbial Growth (Log Cfu/mL) | | |
|---|---|---|---|
| Test Preparations | 0 HOUR | 24 HOUR | 48 HOUR |
| 1% Soybean Oil | <1 | <1 | <1 |
| 2% Soybean Oil | 1.53 | 1.90 | >5.76 |
| 3% Soybean Oil | 1.88 | 4.78 | >5.76 |
| 10% Soybean oil (control) | 2.13 | 5.77 | 8.73 |
| Diprivan | 1.50 | 1.10 | ND |
| Viability Control | 2.11 | 2.95 | >5.76 |

TABLE 4

*C. albicans:* Inoculum Concentration: 2.0 Log Nominal

| | Microbial Growth (Log Cfu/mL) | | |
|---|---|---|---|
| Test Preparations | 0 HOUR | 24 HOUR | 48 HOUR |
| 1% Soybean Oil | 1.60 | <1 | <1 |
| 2% Soybean Oil | 1.56 | 1.28 | 1.26 |
| 3% Soybean Oil | 1.77 | 1.88 | 2.23 |
| 10% Soybean oil (control) | 1.86 | 3.30 | 5.18 |
| Diprivan | 1.55 | 1.45 | 2.05 |
| Viability Control | 1.85 | 1.90 | 1.83 |

Although the lower soybean oil concentrations may be expected to lower the rowth from the higher levels of soybean oil, the lower oil concentrations exhibit growth rates which are lower than the viability control, thereby exhibiting bacteriostatic and, against some of the disclosed microbial strains, bacteriocidal properties. This eliminates the need to utilize a preservative or other anti-microbial agent to prevent comparable growth rates of bacterial contaminants. In particular, as set forth in the tables the preferred embodiments produce antimicrobial effects approximating those described in embodiments described in U.S. Pat. No. 5,637,625 incorporated by specific reference herein. However in contrast to a formulation containing EDTA, the present formulation and the lack of a chelating agent is believed to be safer for patients with an aversion to chelating agents, particularly in large dose-situations.

Another useful aspect of the present invention arises from administering the subject formulation to hyperlipidemic patient, in that the reduced fat content thereof places them at lower risk of triglyceridemia. It is believed this increases the safety of the product when used on critically ill patients with elevated serum triglyceride levels.

From the foregoing description, it will be apparent that the formulation of the present invention has a number of advantages, some of which have been described above, and others which are inherent in the invention. Also, modifications can be made to the formulation without departing from the teachings of the invention. Accordingly, the scope of the invention is only limited as necessitated by the accompanying claims.

What is claimed is:

1. A method of preparing an oil-in-water pharmaceutical composition comprising propofol suitable for parenteral administration comprising:

dissolving propofol in a water-immiscible solvent, thereby forming an oil phase, mixing a phospholipid surfactant and a tonicity modifier with an aqueous phase pharmaceutical vehicle for parenteral administration, thereby forming an aqueous phase, mixing the oil phase with the aqueous phase to form a primary emulsion, recirculating the primary emulsion through a homogenizer to produce microdroplets of said solution of proprfol surrounded by a membrane layer of said surfactant about 160 to about 200 nm in diameter to form a final emulsion, adjusting the pH of the final emulsion using sodium hydroxide to produce a pH of from about 7 to 8.5, and steam sterilizing the emulsion.

2. A method according to claim 1, wherein the water-immiscible solvent is soybean oil.

3. a method in accordance with claim 1, wherein said phospholipid surfactant is lecithin.

4. A method according to claim 1, wherein the tonicity modifier is glycerin.

5. A method in accordance with claim 1 whereing said aqueous pharmaceutical vehicle is Water for Injection, U.S.P.

6. A pharmaceutical composition of propofol for parenteral administration comprising an oil-in-water emulsion in which the oil phase comprises microdroplets of about 160 to 200 nm in diameter comprising propofol dissolved in a water-immiscible solvent and surrounded by a phospholipid surfactant membrane layer and the water phase comprises an aqueous pharmaceutically accetable injectable carrier and a tonicity modifier, wherein propofol comprises at least one weight percent and said solvent comprises from about one to three weight percent, based on the weight of said composition.

7. A pharmaceutical composition in accordance with claim 6, wherein said water-immiscible solvent is soybean oil.

8. A pharmaceutical composition in accordance with claim 6, wherein said tonicity modifier is glycerin.

9. A pharmaceutical composition in accordance with claim 6, wherein said aqueous pharmaceutical vehicle is Water for Injection, U.S.P.

* * * * *